(12) United States Patent
Bill et al.

(10) Patent No.: US 7,740,224 B2
(45) Date of Patent: Jun. 22, 2010

(54) VALVE

(75) Inventors: Markus Bill, St. Wendel (DE); Peter Bruck, Althornbach (DE); Alois Hoffmann, Saarbrucken (DE)

(73) Assignee: Hydac Fluidtechnik GmbH, Sulzbach/Saar (DE)

( * ) Notice: Subject to any disclaimer, the term of this patent is extended or adjusted under 35 U.S.C. 154(b) by 949 days.

(21) Appl. No.: 10/556,340

(22) PCT Filed: Apr. 7, 2004

(86) PCT No.: PCT/EP2004/003698

§ 371 (c)(1),
(2), (4) Date: Jul. 28, 2006

(87) PCT Pub. No.: WO2004/102011

PCT Pub. Date: Nov. 25, 2004

(65) Prior Publication Data

US 2006/0273270 A1     Dec. 7, 2006

(30) Foreign Application Priority Data

May 16, 2003   (DE) ................ 103 23 595

(51) Int. Cl.
  *F16K 31/10* (2006.01)
(52) U.S. Cl. .............. 251/30.04; 251/129.15; 251/129.2; 251/337
(58) Field of Classification Search ............. 251/25, 251/29, 30.01, 30.03, 30.04, 129.15, 129.2, 251/33, 34, 331, 337
See application file for complete search history.

(56) References Cited

U.S. PATENT DOCUMENTS

| | | | | |
|---|---|---|---|---|
| 4,799,645 A | * | 1/1989 | Kramer et al. | 251/30.04 |
| 4,848,721 A | * | 7/1989 | Chudakov | 251/30.02 |
| 4,921,208 A | * | 5/1990 | LaMarca | 251/30.04 |
| 5,072,752 A | * | 12/1991 | Kolchinsky | 137/493 |
| 5,271,599 A | * | 12/1993 | Kolchinsky et al. | 251/30.04 |
| 5,421,545 A | * | 6/1995 | Schexnayder | 251/30.02 |
| 5,865,213 A | * | 2/1999 | Scheffel et al. | 137/614.16 |
| 6,073,652 A | * | 6/2000 | Wilke et al. | 137/596.16 |
| 6,330,798 B1 | | 12/2001 | Stephenson | |
| 6,435,210 B1 | * | 8/2002 | Obersteiner et al. | 137/599.18 |

(Continued)

FOREIGN PATENT DOCUMENTS

DE   199 32 139 A1   1/2001

(Continued)

*Primary Examiner*—Stephen Hepperle
*Assistant Examiner*—Jeremy S Baskin
(74) *Attorney, Agent, or Firm*—Roylance, Abrams, Berdo & Goodman, L.L.P.

(57) ABSTRACT

A valve, in particular, a proportional seat valve or gate valve, includes a valve housing (10) and at least three fluid connections (1, 2, 3) extending through the valve housing. A main piston (18) extends in the valve housing (10). A pilot piston (24) for executing a pilot control (26) may be controlled by a current-carrying magnetic device (28). During an open pilot control (26), fluid from one (2) of the connectors (1, 2), controlled by the main piston (18), reaches the connector (3), controlled by the pilot piston (24), by a cross-sectional narrowing (38) in the main piston (19). The pilot control (26) and, as a result of the corresponding pressure drop, the main piston (18) achieves a control position, controlling both fluid connections (1, 2) with regard to fluid amount.

15 Claims, 3 Drawing Sheets

U.S. PATENT DOCUMENTS 6,869,060 B2 * 3/2005 Barber et al. ............ 251/30.02

FOREIGN PATENT DOCUMENTS

| DE | 199 55 523 A1 | 5/2001 |
|---|---|---|
| DE | 101 06 892 A1 | 9/2002 |
| EP | 0 467 128 A2 | 1/1992 |
| EP | 0 503 188 A2 | 9/1992 |
| EP | 0 893 607 A1 | 1/1999 |
| GB | 901 061 A | 7/1962 |
| JP | 2000009250 | 1/1999 |

* cited by examiner

VALVE

FIELD OF THE INVENTION

The present invention relates to a valve, especially a proportional seat valve or gate valve, having a valve housing and at least three fluid ports extending through the valve housing. A main piston is guided in the valve housing. A pilot valve effects pilot control and can be actuated by a magnet means which can carry current.

BACKGROUND OF THE INVENTION

A generic valve is known from EP-A-0 893 607. This known valve is a magnetically operated drain valve in which, between a load pressure port (P) and a drain port (T) in the lifting module of a forklift, a seat closing element is assigned to the main valve seat and in the closing direction can be pressurized to a variable difference between the drain pressure and the control pressure derived from the load pressure. A pilot valve can be actuated by a magnet means provided with a pilot piston for the control pressure. The main valve formed by the main valve seat and the seat closing element is assigned a pressure compensator with a seat valve sealing function. With the main valve, the seat valve forms a two-way flow regulator independent of the load pressure and leakproof under the load pressure in the closing position of the main valve.

This known approach discloses a structurally simple, magnetically operated drain valve of compact size, with which it is possible to implement a ramp function independently of the load pressure. A ramp function is defined as the possibility of controlling the flow amount depending on lift and independently of pressure. However, the known solution for lowering the load in hydraulic lifting devices does not meet the high demands as desired, specifically achieving a high no-load lowering speed with little leakage and a precise metering of this lowering speed.

Control devices for hydraulically operating lifting means are commercially available, and use directly controlled valves not suitable for high volumetric flow due to the design, so that in general pilot-controlled valves are preferred. In barometrically pilot-controlled valves, an independent pressure supply making available the required pressure for adjusting the main piston is necessary. This pressure is generally 10 to 20 bars, and is often produced by an external supply, for example, the feed pump of the traveling mechanism, in a forklift with an internal combustion engine. In lifts with an electric drive, there is no external supply so that the required control pressure can only be taken from the load pressure. When lowering at no load, the available control pressure can then drop to approximately 2 bars with the result that in no-load lowering the lowering process is hampered.

SUMMARY OF THE INVENTION

An object of the present invention is to provide an improved valve which at low cost permits a high no-load lowering speed with few components in a reliable manner and allows precise metering of the lowering speed with simultaneously little leakage.

This object is basically achieved by a valve in which the pilot control opened, fluid travels from one of the two ports which can be actuated by the main piston by a cross-sectional constriction in the main piston and the pilot control to the third port. The third port can be actuated by the pilot piston. As a result of the accompanying pressure drop, the main piston travels into a respective control position which can actuate the two fluid ports with respect to the amount of fluid. A pilot-controlled proportional seat valve or gate valve is formed which at a very low pilot pressure, for example, <2 bars, already completely opens and thus permits prompt no-load lowering.

If current is supplied to the magnet means to open the pilot control, the main piston is pushed up. The piston lift of the main piston is proportional to the magnet current. Since the position of the main piston always corresponds to the force of the magnet, a valve can be configured permitting precise metering of the lowering speed with simultaneously low leakage for the valve.

In one preferred embodiment of the valve of the present invention, a compression spring is configured between the main piston and the pilot piston. The piston lift of the main piston with the pilot control opened is proportional to the magnet current of the magnet means. The compression spring acting on the main piston reports the position of the main piston back to the pilot piston and consequently to the pilot control so that any disturbing variables, caused by flow forces, for example, can be directly adjusted. The position of the main piston then corresponds to the applied magnet force. When no current is being supplied to the magnet means, flow through the valve is possible due to the compression springs of the two ports with the capacity to be controlled by the main piston as a spring-loaded return valve.

Preferably, the compression spring engages a recess of the main piston into which the cross-sectional constriction in the form of an orifice discharges. On the free end of the compression spring facing the pilot piston, a contact piece is connected to the free end of the pilot piston by a contact ball. The contact ball permits unhampered operation and interaction of the pilot piston with the main piston.

In another embodiment of the valve of the present invention, preferably a selector valve is in the main piston. The selector valve preferably has a cross-sectional constriction. In this version, in the absence of current, the valve can be blocked from one pressure port to another. The ports can be actuated by the main piston. When current is supplied to the magnet means under the corresponding pressure conditions, a volumetric flow between the fluid ports can then be controlled. In one alternative embodiment, the cross-sectional constriction (choke or orifice) can also be located in a fluid-carrying channel downstream from the selector valve in the direction of the interior of the main piston.

In another preferred embodiment of the valve of the present invention, the magnet means has at least one armature, a coil and a pole tube designed as part of a pushing or pulling system. The armature is moved out of or into the pole tube when the coil is supplied with current. When using a pulling system, another compression spring moves the pilot piston in the direction of an opened pilot control. If the "pulling" pole tube is equipped with the additional compression spring keeping the pilot piston in the open position, which corresponds to the fully energized state for the "pushing" pole tube, by switching the magnet means the pilot control and thus the valve can be completely closed. By replacing a "pushing" pole tube with a "pulling" pole tube, a valve which is open without current can therefore be formed from a proportional seat valve which is closed without current. If a pilot spring applies an adjustment force to the pilot piston, this is not absolutely necessary with respect to the operating property of the magnet system. However, it improves the return of the pilot piston and thus the operating dynamics for the entire valve.

In another preferred embodiment of the valve of the present invention, the pilot control is designed as a gate valve in which a pilot piston of cylindrical design at least on its free end is guided to be movable in the longitudinal direction into a corresponding elongated recess in parts of the valve housing. In this way, uniform operating behavior is achieved even under the most varied operating conditions. By maintaining a sufficiently small sealing gap on the pilot piston, the desired forklift tightness can be guaranteed.

In a different embodiment of the valve of the present invention, preferably the pilot control is designed as a seat valve in which, on the free end of the pilot piston, a preferably cone-like closing and sealing part interacts with a seat part formed by parts of the valve housing. In this version, as a seat valve the pilot control is free of leaks. The disadvantage of this version is that the pilot piston is no longer optimally pressure-equalized and is also subject to friction by the seal in its motion. If the pilot control is designed as a valve without a seal, the valve is no longer free of leaks, but inhibitory friction in operation may then be largely precluded. This arrangement ensures that the valve performs its choke function. Preferably, to enhance the sealing on the outside circumference of the pilot piston, additional sealing parts may be provided.

The described valve is especially well-suited for all applications in which a large volumetric flow must be controlled with a low control pressure. This need is often the case in the implementation of the lowering function in electric forklifts.

The proportional seat valve can generally be used as a proportional choke valve for very large volumetric flows. To keep $\Delta_p$ small at high volumetric flows, it may be necessary to enlarge the seat diameter in the valve body. The necessary control pressure for complete opening of the valve thus in fact increases. However, it is always notably less than that of the known barometrically actuated valves.

In one preferred embodiment, the valve of the present invention in a valve system serves the function of an adjustable metering orifice of a flow regulator in conjunction with a pressure compensator. In this configuration, the flow amount can be controlled depending on the lift and independently of the pressure (ramp function). During lowering, the volumetric flow to be managed can be limited in terms of its maximum, serving to enhance reliability.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure and which are diagrammatic and not drawn to scale.

The valve design as claimed in the present invention is detailed below in the drawings in which in diagrammatic form, not drawn to scale.

DETAILED DESCRIPTION OF THE INVENTION

Figure 1:
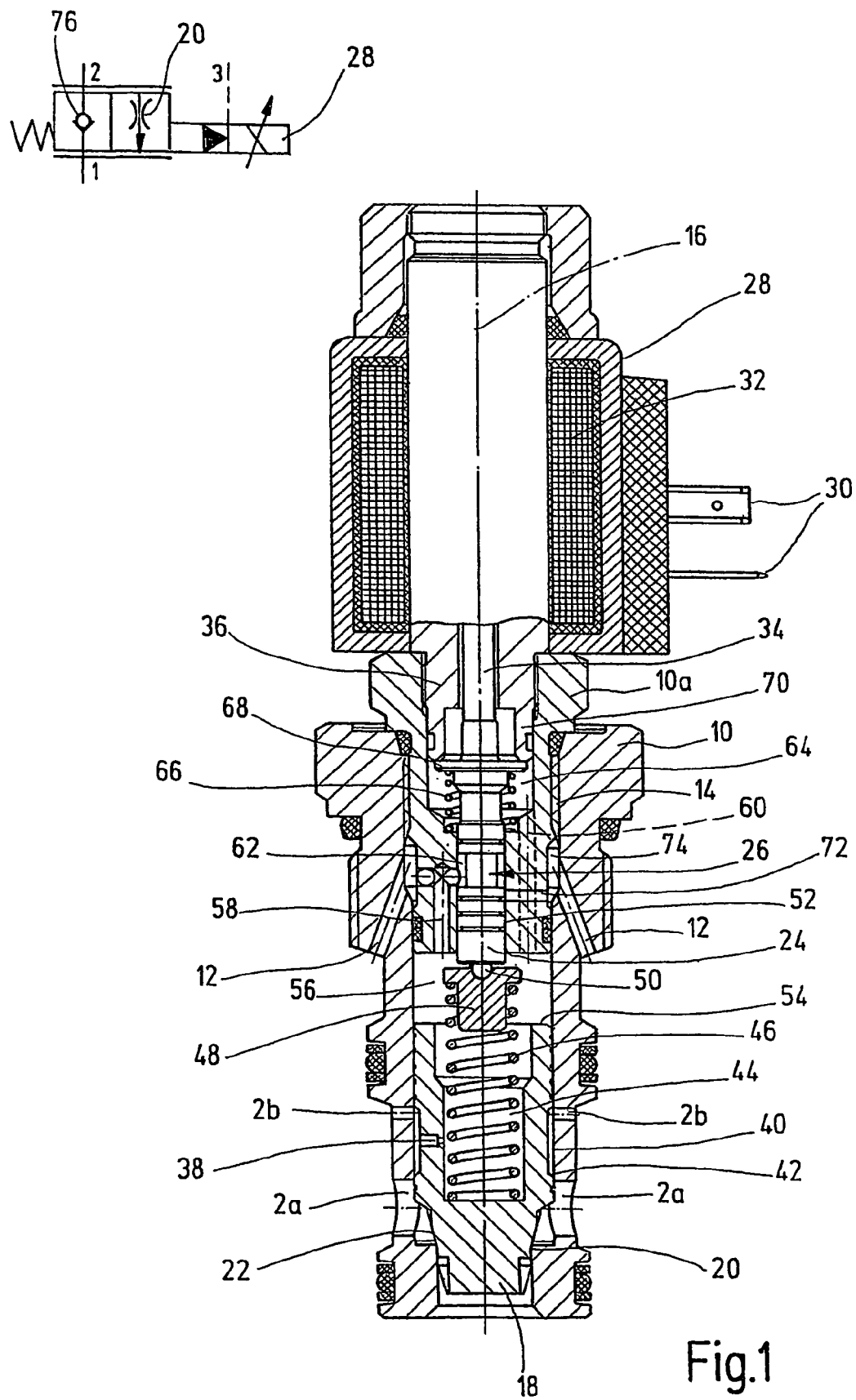
FIG. 1 is a side elevational view in section of a proportional seat valve according to a first exemplary embodiment of the present invention, with a graphic representation of the valve shown at top left thereof.

The valve shown in FIG. 1 in a longitudinal section is a proportional seat value with a valve housing 10. The housing has seals and seal stacks on the outer circumferential side, and is designed as a screw-in cartridge for fixing the valve on other machines or vehicle parts for purposes of controlling a hydraulic circuit (not shown). Furthermore, the valve can also be designed as a kit. The valve housing 10 has three fluid ports 1, 2, 3. One fluid port 1 is on the front engaging on the lower end of the valve housing 10. The other two ports 2 and 3 are configured radially on the valve housing 10 on the outer circumferential side. The fluid port 2 is at two different points 2a, 2b extending radially through the valve housing 10. The third fluid port 3 discharges by way of transverse holes 12 into the interior of the valve housing 10 having in this area a valve insert 10a made with a screw-in bevel 14. In the valve housing 10, a main piston 18 can move axially along the longitudinal axis 16 of the valve and, on its free end and adjacently opposite the fluid port 2a mates with a seat valve 20 on wall parts of the valve housing. For this purpose, the main piston 18 on its free end is provided with a conically extending valve surface 22. Next to the main piston 18 within the valve housing 10, a pilot piston 24 is guided in the longitudinal direction so as to be movable and is part of a pilot control 26.

As viewed in FIG. 1, the valve housing 10 on its top end has a magnet means or electromagnet 28 which can carry current. Attachment plugs 30 connect the magnet to an electrical power source to supply current to a coil winding 32. Coil winding 32 comprises an armature 34 mounted to move in the longitudinal direction within a profiled tube 36 and used to actuate the pilot control 26, especially in the form of a pilot piston 24. This structure of a magnet means 28 is relatively well known in the prior art so that it is not described in detail.

According to the operating diagram as shown in FIG. 1, the main piston 18 is in its closed position, i.e., the seat valve 20 is blocking the fluid path between the fluid ports 1 and 2a. A cross-sectional constriction 38 located radially on the outer circumference of the main piston 18, preferably in the form of an orifice, discharges into a radial recess 40 of the main piston 18. Radial recess 40 extends between the fluid port 2b and a radial projection 42 of the main piston 18 separating the fluid port 2a from the radial recess 40. The main piston 18 is provided with a recess 44 into which the orifice 38 discharges. Within this recess 44 extending in the direction of the longitudinal axis 16, there is a compression spring 46 with its one free end in contact with the bottom of the recess 44 and with its other free end acting on a contact piece 48 movably mounted in the valve housing and biased against pilot piston 24 by compression spring 46. The opposite free end of the contact piece 48 bears a contact ball 50 in a corresponding depression or recess that extends only partially and not through the contact piece, on the top of which the contact ball free end of the pilot piston 24 is supported. In this way, unhampered operation and actuation between the pilot piston 24 and the main piston 18 is achieved, even in the event of possible tilting processes which can be equalized by the contact ball 50.

In the FIG. 1 embodiment as viewed therein in terms of its operation in a conventional operating diagram at top left, the fluid ports 1, 2, and 3 correspond to the ports as shown in the valve cross section. The pilot control 26 is designed as a gate valve in which the cylindrically configured pilot piston 24 at least on its free end is guided to be movable in the longitudinal direction in a corresponding longitudinal recess 52 which is circular in transverse cross section in parts of the valve housing 10 in the form of a valve insert 10a. The pilot piston 24 on its outer circumferential side is conventionally enclosed by pressure relief grooves which at least partially ensure leak-tightness in this area of the pilot control 26. Between the underside of the valve insert 10a and the upper terminating end of the main piston 18 forming its back 54, the inner circumferential side of the valve housing 10 borders the control chamber 56 into which longitudinal channels 58, 60 of the valve insert 10a discharge. One longitudinal channel 58 at its other or upper end discharges into an annular recess 62 of the pilot piston 24. The other longitudinal channel 60 with its other or upper free end discharges into an annular chamber 64 in which another compression spring 66 is supported. The lower spring end is on the inner circumference of the valve insert 10a, the other or upper spring end being on the radial widening 68 of the pilot piston 24. In the illustrated operating diagram of FIG. 1, the radial widening 68 is supported with its outer flange on the front end of the magnet housing 70 inserted at this point in the valve insert 10a by a screw-in section. A radial annular channel 72 discharges into a radial chamber 74 between the inner circumferential side of the top end of the valve housing 10 and the outer circumferential side of the valve insert 10a in this area. In turn, the fluid port 3 (holes 12) discharges into this radial chamber 74. On the opposite end in the illustrated operating position shown in FIG. 1, the annular channel 72 is closed by the outside circumference of the pilot piston 24. The actuated pilot piston 24 is pressed down by the magnet means 28 when viewed in the direction of FIG. 1, capable of establishing a fluid-carrying connection between the control chamber 56, the longitudinal channel 58, the annular recess 62, the annular channel 72, the radial chamber 74, and the fluid port 3 by way of channel-shaped transverse holes 12.

For the sake of better understanding, at this point the proportional seat valve shown in FIG. 1, specifically intended for use in hydraulically operating lifting means, will be described in detail using a working example. If the magnet means 28 is supplied with current by the attachment plug 30, the armature 34 under the action of the field of the coil winding 32 migrates out of the pole tube 36, and in the process actuates the pilot piston 24 of the pilot control 26 against the action of the other compression spring 66. The reset force of spring has the tendency to keep or bias the radial widening 68 in contact with the lower end of the magnet housing 70. The magnet force is sufficient to open the pilot control 26 against the action of the other compression spring 66, with the pilot oil flowing from the load port 2 by the respective connecting point 2b into the radial recess 40 of the main piston 18. From there, the pilot oil flows through the cross-sectional constriction 38 (orifice) into the recess 44 of the main piston 18 in which the compression spring 46 is mounted. From there the pilot oil flows into the control chamber 56 and then by the longitudinal channel 58 and the annular recess 62 in the pilot piston 24 into the annular channel 72. From channel 72 the pilot end flows by the radial chamber 74 and the oblique holes 12 to the fluid port 3. In the process the pressure drops on the rear 54 of the main piston 18 and by the load pressure acting on the annular surface between the outside piston diameter and the valve seat diameter of the main piston 18 at the location of its seat valve 20, the main piston is pushed up against the action of the compression spring 46, as viewed in FIG. 1. This piston lift of the main piston 18 is proportional to the magnetic current. The compression spring 46 located in the main piston 18 reports the position of the main piston 18 back to the pilot piston 24 so that disturbing variables, such as, for example, the flow forces, can be adjusted in this way. The position of the main piston 18 thus always corresponds to the magnetic force of the magnet means 28 in the current-carrying state. Without current, the main piston 18 assumes its position shown in FIG. 1, and in this position as a result of the compression spring 46 the valve acts like a spring-loaded return valve 76 relative to the control of possible fluid flow between the fluid ports 1 and 2.

With this configuration, a pilot-controlled proportional seat valve is implemented which at a very low pilot pressure, for example, <2 bars already completely opens. This operation permits rapid no-load lowering so that its use is of interest especially in electrically operated forklifts which do not have an external supply necessary to ensure the required pressure for setting the main piston in barometrically pilot-controlled valves, as they are known in the prior art.

The pilot spring in the form of the other compression spring 66 is not absolutely necessary, but, as already described, it improves the return of the pilot piston 24 and the dynamics of the valve as a whole. The pilot control 26 in FIG. 1 is designed as a gate valve, the best solution for uniform operating behavior under different operating conditions. This solution is accompanied by the disadvantage that the valve shown in FIG. 1 consequently is subject to leakage. By maintaining a sufficiently small sealing gap on the pilot piston 24, the desired forklift tightness can be ensured.

The pole tube 26 used in FIG. 1 is designed as a pushing system in which the armature 34 emerges from the pole tube 36 when the coil winding 32 is supplied with current. In "pulling" systems, that is in a "pulling" pole tube, the armature 34 moves into the pole tube 36. If the "pulling" pole tube is equipped with a compression spring (not shown) biasing the pilot piston 24 towards the open position corresponding to the state of full current supply for the pushing pole tube 36, by switching the magnet means 28 the pilot control 26 and thus the valve can be completely closed. By replacing a "pushing" pole tube 36 by a "pulling" pole tube, a valve which is open without current can thus easily be configured from a proportional seat valve which is closed without current, if the requirements of practical application make this necessary.

Figure 3:
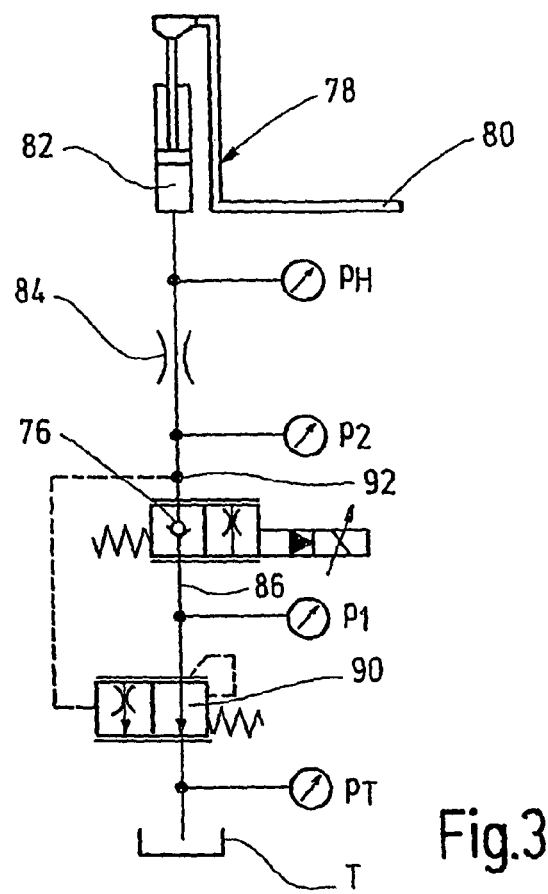
FIG. 3 is an operating diagram that shows the use of the valve of FIG. 1 for a load lowering of forklift units with a maximum volumetric flow limitation and with load compensation.

FIG. 3 shows one example of an application of the proportional seat valve shown of FIG. 1 for a hydraulically operating lifting means 78. The hydraulic lifting means 78 has a load fork 80 of conventional design which can be raised and lowered by an actuator cylinder 82. For the sake of clarity of illustration, the behavior of the lifting frame of the lifting means 78 is shown here as a choke 84 in terms of its hydraulic behavior. Moreover, the piston side of the actuator cylinder 82 can be connected to the tank T by the connecting line 86. The symbolically shown pressure gauges with designations $P_H$, $P_2$, $P_1$, and $P_T$ within the scope of a test set-up would permit tapping of pressure valves in individual travel positions of the lifting means 78 within the connecting line 86. As FIG. 3 furthermore shows, a known pressure compensator 90 with a choke function is connected to the connecting line 86, and is controlled by the prevailing pressure in the connecting line 86 by the connecting point 92. In this way, as shown in FIG. 3, a valve system is implemented with a valve as shown in FIG. 1 and the known pressure compensator 90. An adjustable metering orifice of a flow regulator is implemented. The proportional seat valve shown in FIG. 1 can be used in this way as a proportional choke valve for very large volumetric flows. With the illustrated valve system shown in FIG. 3, the maximum volumetric flow can be limited when the load fork 80 is being lowered (with or without a load). This arrangement benefits reliability during operation of the lifting means. In particular, with this solution at a low control pressure a large volumetric flow can be controlled.

Figure 2:
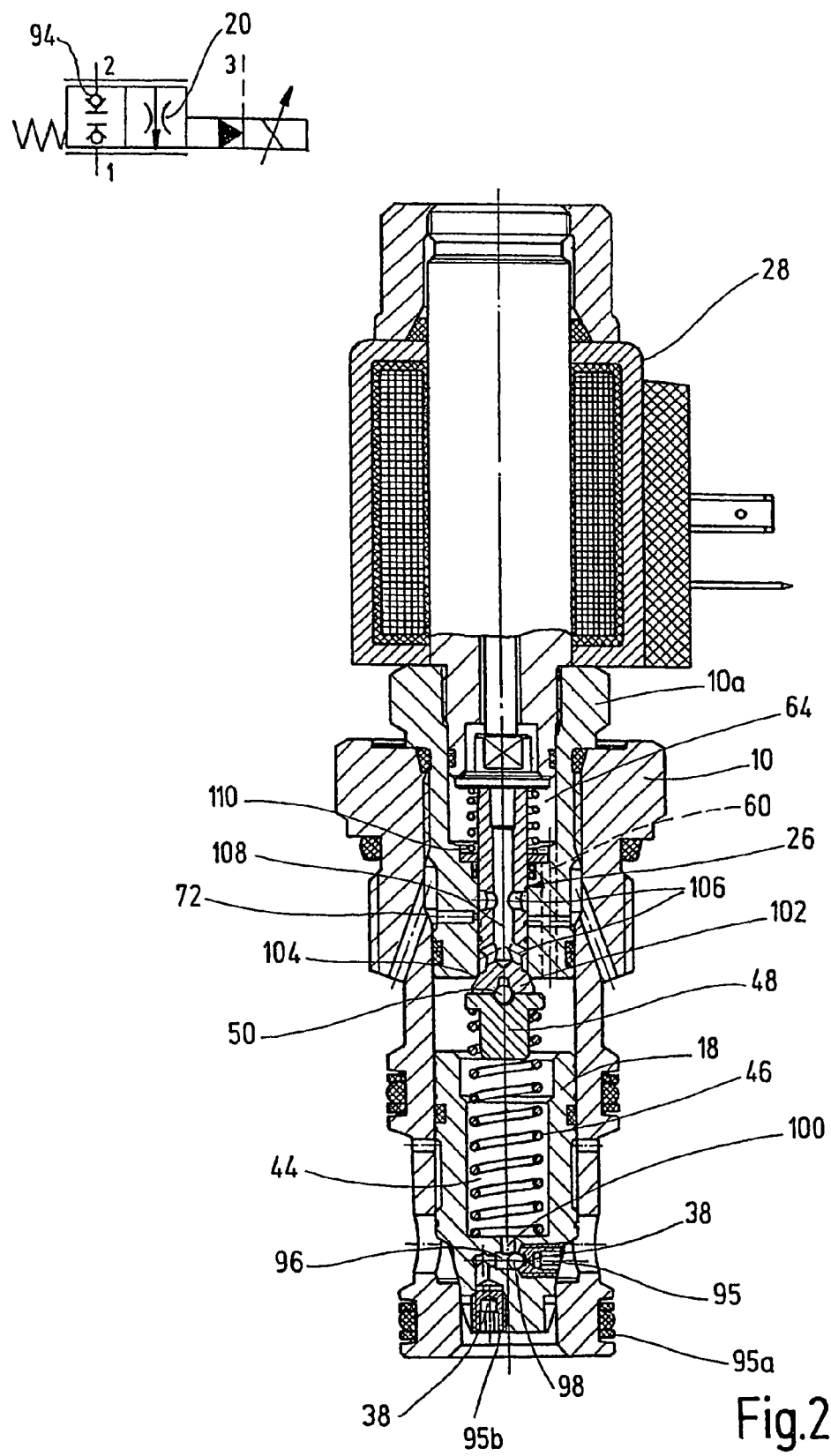
FIG. 2 is a side elevational view in section of a proportional seat valve according to a second exemplary embodiment of the present invention, with a graphic representation of the valve shown at top left thereof.

The second embodiment shown in FIG. 2 constitutes a version of the embodiment shown in FIG. 1, and accordingly is only explained to the extent it differs significantly from the embodiment in FIG. 1. In this respect, the same reference numbers as in FIG. 1 are used for the same parts. What has been stated previously also applies in this respect to the modified embodiment shown in FIG. 2.

In the embodiment as shown in FIG. 2, on the lower front end of the main piston 18 there is a selector valve 95. The selector valve 95 has a cross-sectional constriction. The orifice function is present twice in two throughflow directions from 1 to 2 and vice versa relative to the fluid ports. The selector valve 95 has a valve ball 98 which can be moved in a transverse channel 96 and which, depending on the incident fluid flow direction from the fluid port 1 to 2 or vice versa, on the one hand blocks the fluid connection point of one selector valve insert 95a and of the other selector valve insert 95b with their respective cross-sectional constrictions 38. The transverse channel 96 in the longitudinal direction of the valve has a longitudinal channel 100 which discharges into the recess 44 in the main piston 18 with the compression spring 46. In the embodiment shown in FIG. 2, the pilot control 26 is designed as a seat valve with a seal. For this purpose, the pilot piston 24 on its bottom free end has a cone-shaped closing and sealing part 102 interacting with the seat part 104 on the bottom end of the valve insert 10a. Instead of the longitudinal channel 58, the modified solution shown in FIG. 2 in the pilot piston 24 has transverse channels 106 connected to one another to carry fluid by a central longitudinal channel 108. In this way, with the pilot control 26 opened, the fluid flow from the fluid port 2 to the fluid port 3 is ensured. Furthermore, the pilot piston 24 on the outer circumferential side has a sealing system 110 within the annular chamber 64. In the illustrated version shown in FIG. 2, the pilot control 26 is free of leaks. The pilot piston 24 no longer is optimally pressure-equalized, but rather is also made subject to friction by the sealing system 110. If the seal are omitted, the disadvantage of friction would not arise. However, this valve would then no longer be free of leaks.

With the valves shown in FIGS. 1 and 2, high no-load lowering speeds can be achieved in hydraulic lifting means with simultaneously precise metering of the lowering speed and with little leakage.

Figure 4:
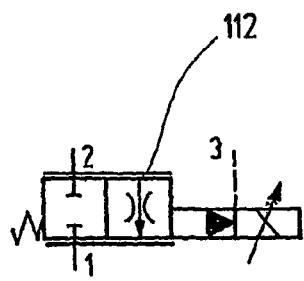
FIG. 4 is an enlarged side elevational view in section through the lower part of a proportional gate valve according to a third exemplary embodiment of the present invention with graphic representation of the valve at top left thereof.
Figure 4:
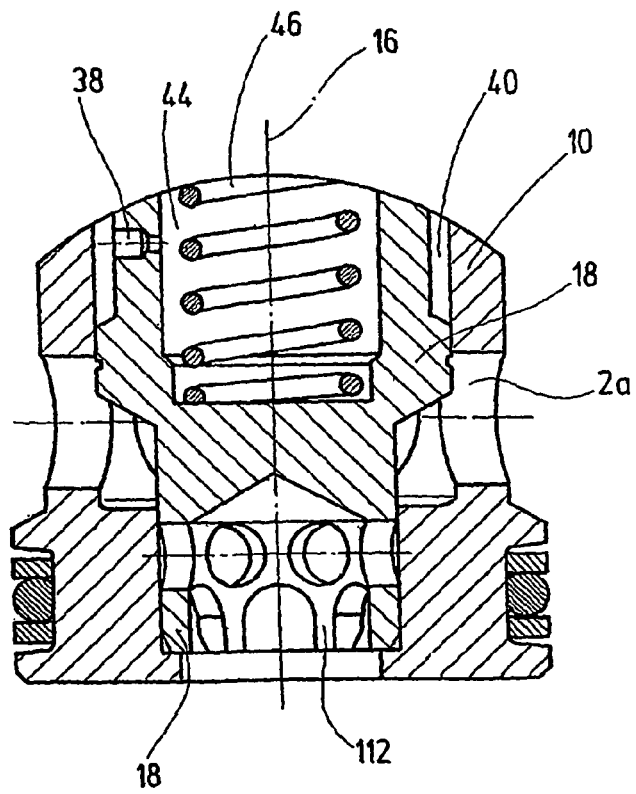

FIG. 4 relates to another modified valve embodiment compared to the illustrated versions in FIGS. 1 and 2. FIG. 4 relates to the lower valve part designed as a gate valve, especially a proportional gate valve. Instead of the previously described conical valve seat 20, the free end of the main piston 18 is made cylindrical, and is guided in a cylindrical inner circumferential surface of the lower end of the valve housing 10. With the main piston 18 raised, in this way the fluid-carrying choked connection between the valve port 2a and the free fluid entry side is established by the fluid-carrying part 112 on the front end of the valve housing 10. The corresponding operating diagram is shown at top left of FIG. 4. The pilot control for this valve version is designed as a gate valve is executed accordingly, as described in the foregoing for the valve versions as shown in FIGS. 1 and 2.

While various embodiments have been chosen to illustrate the invention, it will be understood by those skilled in the art that various changes and modifications can be made therein without departing from the scope of the invention as defined in the appended claims.

What is claimed is:

1. A valve, comprising:
a valve housing;
at least first, second and third fluid ports extending through said valve housing;
a main piston guided for movement in said valve housing;
a pilot control designed as a seat valve with a pilot piston actuated by an electromagnet to move to an open position where fluid flows from one of said first and second fluid ports, actuated by said main piston, via a cross-sectional constriction orifice in said main piston and via said pilot piston to said third fluid port actuated by said pilot piston, said main piston traveling to a respective control position as a result of an accompanying pressure drop to actuate said first and second fluid ports relative to amounts of fluid, piston lift of said main piston with said pilot piston in said open position being proportional to current supplied to said electromagnet, a free end of said pilot piston having a closing and sealing part interacting with a seat part on a part of said valve housing;
a compression spring between said main piston and said pilot piston and received in a main piston recess in said main piston, said cross-sectional constriction orifice discharging into said main piston recess; and
a contact piece on a free end of said compression spring adjacent said pilot piston, said contact piece connected to a free end of said pilot piston by a contact ball.

2. A valve according to claim 1 wherein
a selector valve is in said main piston, and has a cross-sectional constriction.

3. A valve according to claim 1 wherein
said electromagnet comprises at least one armature, a coil and a pole tube with said armature being one of moved out of said pole tube and moved into said pole tube when said coil is supplied with current.

4. A valve according to claim 3 wherein
said armature is moved into said pole tube when said coil is supplied with current; and
another compression spring biases said pilot piston towards said closed position thereof.

5. A valve according to claim 1 wherein
additional sealing parts of a sealing system are on an outer circumference of said pilot piston.

6. A valve according to claim 1 wherein
said contact piece comprises a contact piece recess receiving said contact ball, said contact piece recess only extending partially into and not through said contact piece.

7. A valve according to claim 1 wherein
said contact piece is movably mounted in said valve housing, and is biased against said pilot piston by said compression spring.

8. A valve system, comprising:
a valve including
a valve housing;
at least first, second and third fluid ports extending through said valve housing;
a main piston guided for movement in said valve housing;
a pilot control designed as a seat valve with a pilot piston actuated by an electromagnet to move to an open position where fluid flows from one of said first and second fluid ports, actuated by said main piston, via a cross-sectional constriction orifice in said main piston and via said pilot piston to said third fluid port actuated by said pilot piston, said main piston traveling to a respective control position as a result of an accompanying pressure drop to actuate said first and second fluid ports relative to amounts of fluid, piston lift of said main piston with said pilot piston in said open position being proportional to current supplied to said electromagnet, a free end of said pilot piston has a closing and sealing part interacting with a seat part on a part of said valve housing, a compression spring between said main piston and said pilot piston and received in a main piston recess in said main piston, said cross-sectional constriction orifice discharging into said main piston recess, and a contact piece on a free end of said compression spring adjacent said pilot piston, said contact piece connected to a free end of said pilot piston by a contact ball; and a pressure compensator, coupled to said valve, forming an adjustable metering orifice of a flow regulator.

9. A valve system according to claim 8 wherein a selector valve is in said main piston, and has a cross-sectional constriction.

10. A valve system according to claim 8 wherein said electromagnet comprises at least one armature, a coil and a pole tube with said armature being one of moved out of said pole tube and moved into said pole tube when said coil is supplied with current.

11. A valve system according to claim 10 wherein said armature is moved into said pole tube when said coil is supplied with current; and another compression spring biases said pilot piston towards said closed position thereof.

12. A valve system according to claim 8 wherein additional sealing parts of a sealing system are on an outer circumference of said pilot piston.

13. A valve system according to claim 8 wherein said contact piece comprises a contact piece recess receiving said contact ball, said contact piece recess only extending partially into and not through said contact piece.

14. A valve system according to claim 8 wherein said contact piece is movably mounted in said valve housing, and is biased against said pilot piston by said compression spring.

15. A valve, comprising:

a valve housing;

at least first, second and third fluid ports extending through said valve housing;

a main piston guided for movement in said valve housing;

a pilot control designed as a gate valve with a pilot piston actuated by an electromagnet to move to an open position where fluid flows from one of said first and second fluid ports, actuated by said main piston, via a cross-sectional constriction orifice in said main piston and via said pilot piston to said third fluid port actuated by said pilot piston, said main piston traveling to a respective control position as a result of an accompanying pressure drop to actuate said first and second fluid ports relative to amounts of fluid, piston lift of said main piston with said pilot piston in said open position being proportional to current supplied to said electromagnet, said pilot piston being cylindrical at least on a free end thereof and being movable in a longitudinal direction in a corresponding longitudinal recess in a part of said valve housing;

a compression spring between said main piston and said pilot piston and received in a main piston recess in said main piston, said cross-sectional constriction orifice discharging into said main piston recess; and a contact piece on a free end of said compression spring adjacent said pilot piston, said contact piece connected to a free end of said pilot piston by a contact ball.

* * * * *